United States Patent [19]

Scott

[11] 4,259,954

[45] Apr. 7, 1981

[54] WASH BOTTLE AND METHOD FOR AMELIORATING HEMORRHOIDS

[76] Inventor: Robert S. Scott, 67C Joyce Ellen La., Ferguson, Mo. 63135

[21] Appl. No.: 77,005

[22] Filed: Sep. 19, 1979

[51] Int. Cl.³ ............................................. A61M 7/00
[52] U.S. Cl. .................................... 128/248; 128/232; 222/213
[58] Field of Search ............... 128/248, 249, 250, 251, 128/232, 231; 222/206, 211, 212, 213

[56] References Cited

U.S. PATENT DOCUMENTS

| | | | |
|---|---|---|---|
| 797,365 | 8/1905 | Meinecke | 128/232 |
| 3,705,668 | 12/1972 | Schwartzman | 222/213 |
| 4,140,120 | 2/1979 | Yamauchi | 128/232 |

*Primary Examiner*—John D. Yasko
*Attorney, Agent, or Firm*—Senniger, Powers, Leavitt and Roedel

[57] ABSTRACT

A wash bottle adapted for use in irrigating body tissue surfaces. The bottle comprises a container constituted of flexible resilient material having a mouth. A closure for the mouth is detachable to permit filling of the container with a wash liquid. A nozzle on the closure permits delivery of wash liquid from the container. Conduit means inside the closure and in communication with the nozzle provide for delivery of wash liquid to the nozzle. Valve means comprise a valve seat at an inlet of the conduit means and a stem attached at one end to a portion of a wall of the container and having a free end engageable with the valve seat to prevent entry of liquid into the conduit means from the interior of the container when the container is in an unstressed condition. Said portion of the wall is movable outwardly on squeezing the container to move the stem away from the seat, thereby opening the conduit means to the interior of the container and resulting in the delivery of wash liquid out through the conduit means and nozzle when the bottle is in an inverted position.

18 Claims, 6 Drawing Figures

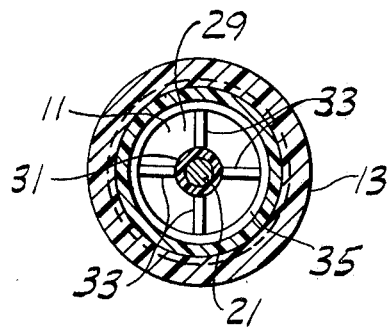
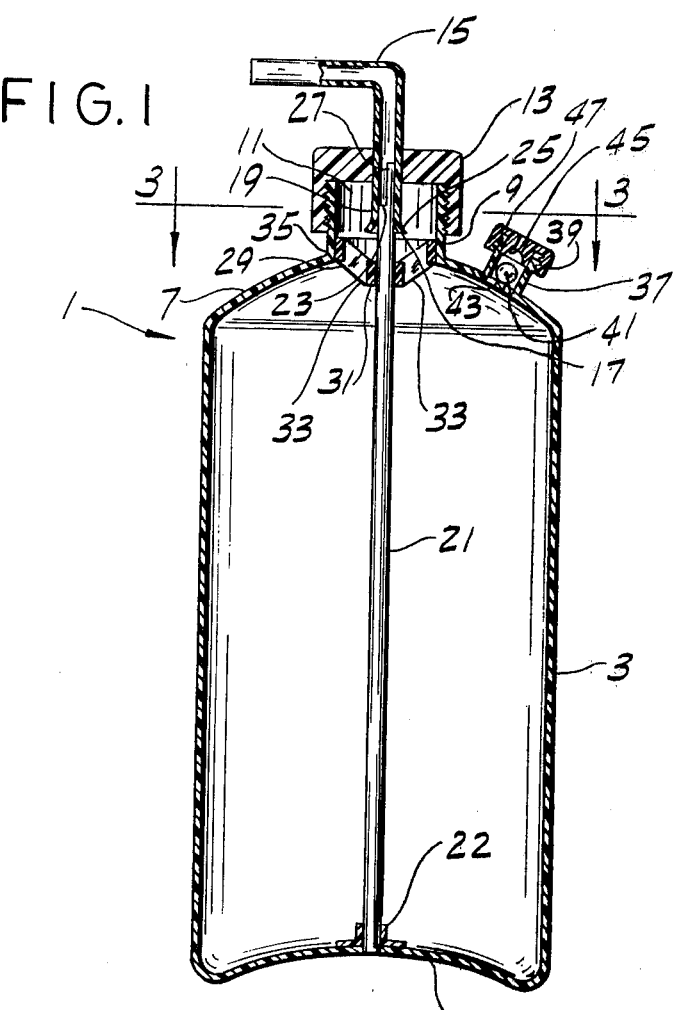
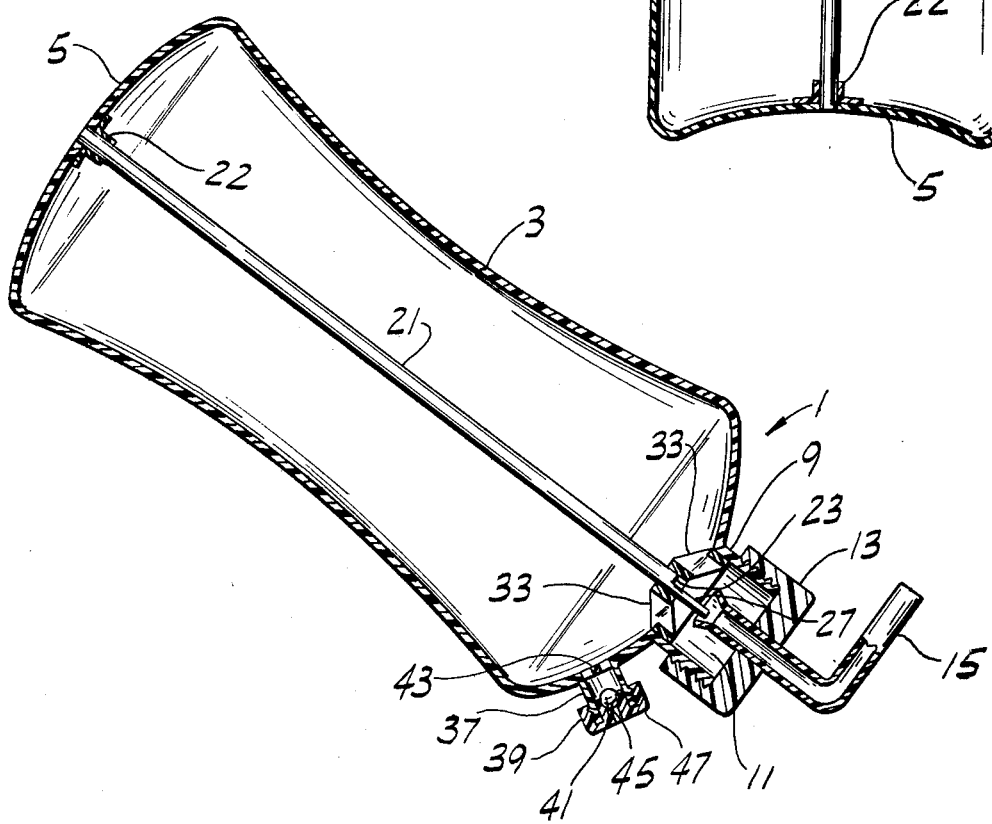

WASH BOTTLE AND METHOD FOR AMELIORATING HEMORRHOIDS

BACKGROUND OF THE INVENTION

This invention relates to the field of devices for ameliorating hemorrhoidal conditions and more particularly to a novel wash bottle and method for removing fecal matter from the anal area by irrigation thereof.

Hemorrhoidal conditions are aggravated by removal of fecal material from the anal area by the conventional method of wiping with toilet paper. Because of its abrasive character, even the softest of toilet paper causes irritation to the tender anal tissue surfaces affected by hemorrhoids. In view of the prevalence of hemmorrhoidal conditions there has been a serious need for devices or techniques which permit cleansing of the anal area without aggravating the irritation and inflammation caused by hemorrhoids.

SUMMARY OF THE INVENTION

Among the several objects of the present invention, therefore, may be noted the provision of a novel device for cleansing the anal area with minimal irritation thereof; the provision of such a device which is effective for cleansing an anal area affected by hemorrhoids without aggravation of that condition; the provision of such a device which is operative to irrigate the anal area with a cleanisng liquid that does not aggravate hemorrhoidal irritation; the provision of such a device which is uniquely adapted for use in the orientation necessary for cleansing the anal area, the provision of such a device which is effective for such purpose without the cleansing liquid either leaking onto the hands or otherwise by-passing the stream applied to the anal area; and the provision of a method for ameliorating hemorrhoids by cleansing the anal area without the abrasive effect of the conventional application of toilet paper or other solid state materials.

Briefly, therefore, the present invention is directed to a wash bottle adapted for use in irrigating body tissues surfaces. The bottle comprises a container constituted of flexible resilient material and having a mouth. There is a closure of the mouth detachable to permit filling of the container with a wash liquid and a nozzle on the closure for delivery of wash liquid from the container. Conduit means inside the closure and in communication with the nozzle provide for the delivery of wash liquid to the nozzle. Valve means comprise a valve seat at an inlet end of the conduit means and a stem attached at one end to a portion of a wall of the container and having a free end engageable with the valve seat to prevent entry of the liquid into the conduit means from the interior of the container when the container is in an unstressed condition. Said portion of the wall is movable outwardly on squeezing the container to move the stem away from the seat, thereby opening the conduit means to the interior of the container and resulting in delivery of the wash liquid out through the conduit means and nozzle when the bottle is in an inverted position.

The invention is further directed to a method for ameliorating hemorrhoids by removal of fecal matter from the area surrounding the anus without the use of paper or other solid state material. The method comprises positioning in an inverted orientation adjacent the anal area a wash bottle comprising a container constituted of flexible resilient material having a discharge nozzle for delivery of wash liquid when the bottle is in an inverted position and an internal valve that is opened by movement of a valve stem away from a valve seat on deformation of the container by squeezing thereof and which is closed by return of the container to its original configuration in an unstressed condition. The wash bottle is squeezed so as to open the valve and deliver a stream of wash liquid out through the tube; and the stream is directed to areas of body tissue bearing fecal matter so as to irrigate such areas and remove the fecal matter therefrom.

DESCRIPTION OF THE DRAWINGS

FIG. 1 is an elevation in section of the wash bottle of the invention; and

FIG. 2 is a view similar FIG. 1 showing the wash bottle in position for operation to cleanse with anal area; and FIG. 3 is a section taken along the line 3—3 of FIG. 1.

DESCRIPTION OF THE PREFERRED EMBODIMENT

Figure 4:
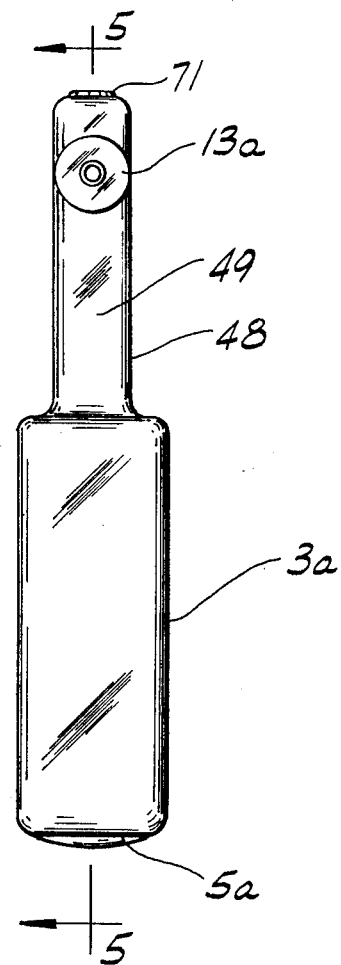
FIG. 4 is an elevation of an alternative embodiment of the wash bottle of the invention.

In accordance with the present invention, a novel wash bottle and method are provided whereby the body tissue in the anal area can be cleansed of fecal material without irritation of already inflamed tissue. By use of the wash bottle in accordance with the method, the anal area is irrigated with a wash liquid, typically warm water, which is impinged on the body tissue with a force that is sufficient for removing fecal matter but which is not so great as to cause irritation. By this method a substantial proportion of the fecal matter is directly removed, and irrigation of the anal area with water has a lubricating effect which permits removal of residual fecal matter by toilet paper without the abrasion incurred in the conventional use of paper. The wash bottle is uniquely adapted for operation in a position necessary for cleansing of the anal area without the wash liquid either leaking onto the hands or otherwise bypassing the stream that is impinged on the body tissue. Use of the novel wash bottle and method of the invention is, therefore, effective for ameliorating hemorrhoidal conditions.

Referring now to FIG. 1 there is shown at 1 a wash bottle comprising a cylindrical container 3 having a bottom wall 5, a head 7, and a neck 9 leading to a mouth 11 centrally located of the head substantially on the axis of the container. The container is constituted of a flexible resilient material and is also preferably transparent or translucent so that the operator can visually observe the liquid level therein. Conveniently, a plastic material such as polyethylene is used as the material of construction.

Neck 9 is threaded to receive a screw cap type closure 13. Extending through screw cap 13 is a delivery tube 15, the inner end of which constitutes a conduit that termintes inside neck 9 and is essentially coaxial with the container, and the outer end of which comprises a discharge nozzle bent at 90° angle to that axis. At the inner end of tube 15 is a valve 17 which comprises a valve seat 19 in the tube and a solid stem 21 attached at one end to bottom wall 5 and having a free end 23 which is engageable with seat 19 to close the tube when the container is in its normal unstressed condition. The fixed end of stem 21 is cemented in a hole in wall 5 and secured by flanged collar 22 on the inside of the bottle wall. The internal surface of the inner end of tube 15 may serve as valve seat 19 through a simple interference fit with end 23 of stem 21 in which event the inner end of the tube is preferably flaired slightly as at 25 so as to permit smooth entry of the stem into the tube. For the same purpose, it is also preferred that end 23 be a reduced end as indicated at 27. This feature not only facilitates entry but modulates opening and closing of the valve on squeezing and release of the bottle.

When container 3 is squeezed, the portion of wall 5 to which stem 21 is attached moves away from seat 19, thereby opening valve 17 and permitting expulsion of liquid when the bottle is in the inverted position. Release of squeezing pressure permits the bottle to return to an unstressed condition, whereupon free end 23 of stem 21 engages seat 19 to close the valve.

Gross offset of stem 21 and tube 15 is prevented by a valve stem guide 29 which comprises a spider shaped member comprising an inner collar 31, for guiding the stem, attached by ribs 33 to an outer collar 35 which is in turn attached to the inside base of neck 9.

A vent 37 is provided on head 7 in proximity to mouth 11 and includes a check valve 39 comprising a ball 41, an inner stop 43, and a seat 45 contained within a screw cap 47 attached to the outer end of the vent. Stop 43 is configured to permit passage of air when ball 41 is in engagement therewith but seat 45 is configured to prevent passage of air when it is engagement with the ball. Thus, when the bottle is squeezed for expelling liquid through tube 15, ball 41 moves into engagement with seat 45 to prevent leakage of fluid out the vent while upon withdrawal of squeezing pressure the resilient container returns to its unstressed state, thereby drawing air in through vent 37 and causing ball 41 to be moved into engagement with stop 43 in which position air can enter the container to replace the liquid expelled during the squeezing portion of the cycle. A continued pumping action can thereby be achieved without either leakage of liquid or reduction of pressure inside of the container.

To provide a stream of the desired volume and intensity the outlet end of tube 15 should have a diameter of between about 1/32" and 3/16". Preferably the diameter is approximately 1/16".

FIG. 2 illustrates the inverted position in which the wash bottle is operated in accordance with the method of the invention for irrigation of body tissue in the anal area to remove fecal matter therefrom.

Figure 5:
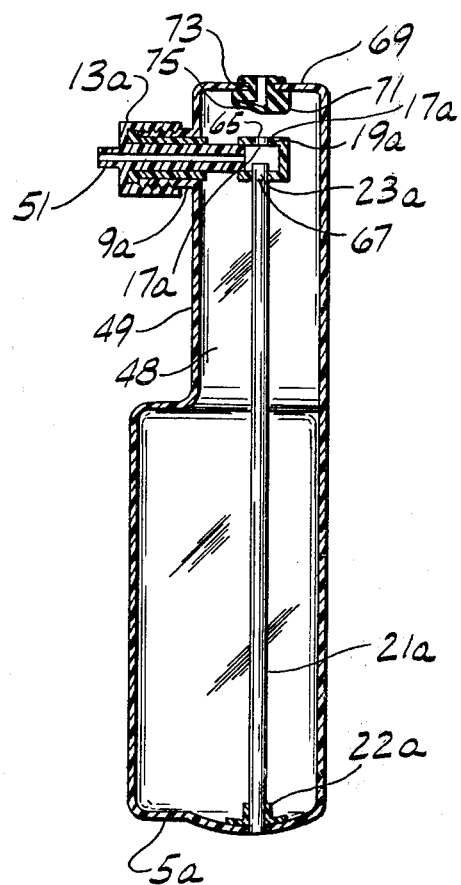
FIG. 5 is a section along the line 5—5 of FIG. 3.
Figure 6:
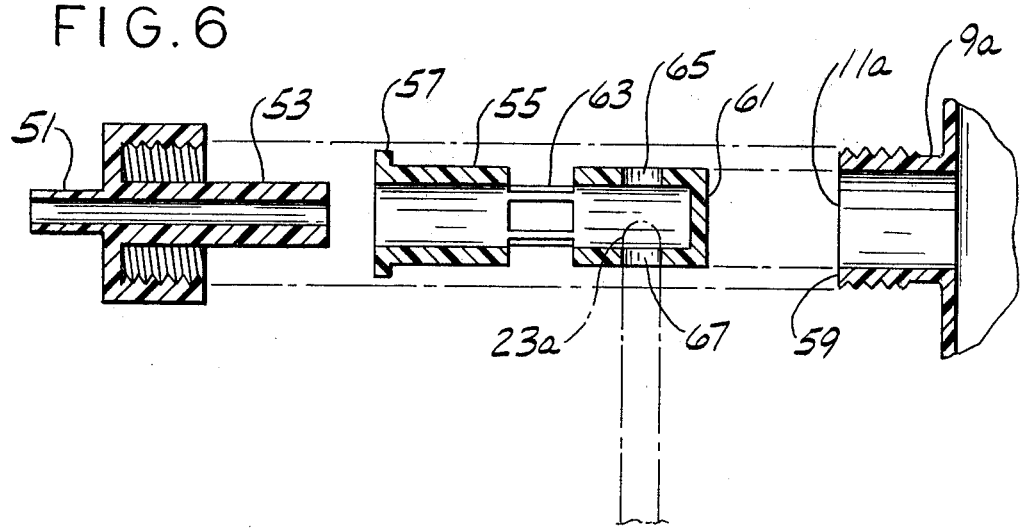
FIG. 6 is detailed view showing the closure, nozzle conduit means and valve means of the embodiment of FIGS. 4 and 5.

In the alternative configuration illustrated in FIGS. 3 to 5 the bottle comprises a container 3a that is again constituted of flexible, resilient, preferably translucent, material but is of generally rectangular cross-section having a bottom wall 5a and a reduced rectangular cross-section upper portion 48. A neck 9a on a side wall 49 of upper portion 48 leads to a mouth 11a the container.

Neck 9a is threaded to receive a screw cap type closure 13a having an integral discharge nozzle 51 thereon whose diameter is in the same range as the discharge end of tube 15 of FIG. 2. Also integral with the screw cap is an internal tube 53 which is in communication with nozzle 51, terminates inside of neck 9a and is essentially perpendicular to the axis of upper portion 47. Tube 53 is adapted for a telescopic fit within a tubular member 55 to constitute a sleeve therein and provide an assembly which affords a conduit for delivery of liquid from the interior of the bottle to discharge nozzle 51. Tubular member 55 is adapted to fit within neck 9a and has a flange 57 at its outer end which is engageable with the outer rim 59 of the neck to limit inward travel of member 55 and permit the fixing of its position when screw cap 13a is in its closed position. Flange 57 is preferably cemented to rim 59 to fix tubular member 55 in place.

Tubular member 55 has a closed inner end 61. Ports 63 in the side wall thereof permit filling of the container when the screw cap is removed. When screw cap 13a is in the closed position, sleeve 53 is oriented within tubular member 55 so as to close ports 63.

In the side wall of tubular member 55, located inwardly port 63 and of the inner end of sleeve 53, are linearly aligned openings 65 and 67. A valve 17a is comprised of a seat 19a defined by port 65 and a solid stem 21a that is attached at one end to bottom wall 5a and has a free end 23a which extends through port 67 to engage seat 19a. Port 67 serves as a guide for the valve. The fixed end of stem 21a is cemented in a hole in wall 5a and secured by a flanged collar 22a on the inside of the bottle wall.

In top wall 69 of container 3a is a vent 71 comprising a flanged rubber tube 73 extending through an aperture in the wall and a rubber flapper valve 75. Valve 75 is closed by internal pressure when the container is squeezed but opens to admit air when the internal pressure falls below atmosphere as the bottle returns to its unstressed condition after squeezing.

Operation of the bottle is essentially identical to that of FIGS. 2 and 3. Thus, the bottle is conveniently utilized in an inverted position with the axis of the container at approximately 45° to the vertical. Squeezing of the container withdraws free end 23a from seat 19a, opening valve 17a and permitting flow out through sleeve 53 and nozzle 51. Release of squeezing pressure allows valve 17a to reseat and close.

In accordance with the method of the invention, the wash bottle is filled with a wash liquid, typically warm water, inverted to permit expulsion of water therefrom, and positioned so that the stream emanating from the tube is directed towards the areas of body tissue to be cleansed. Conveniently the filled bottle is placed between the legs, and then squeezed to direct the liquid to the desired area, thereby irrigating such areas and removing fecal matter therefrom. Irrigation of those areas has a lubricating effect which facilitates subsequent removal of residual fecal matter by toilet paper without abrasion of sensitive body tissue.

In view of the above, it will be seen that the several objects of the invention are achieved and other advantageous results attained.

As various changes could be made in the above methods and products without departing from the scope of the invention, it is intended that all matter contained in the above description or shown in the accompanying drawings shall be interpreted as illustrative and not in a limiting sense.

What is claimed is:

1. A wash bottle adapted for use in irrigating body tissue surfaces comprising a container constituted of flexible resilient material having a mouth, a closure for the mouth detachable to permit filling of the container with a wash liquid, a nozzle on said closure for delivery of wash liquid from the container, conduit means inside the closure and in communication with the nozzle for delivery of wash liquid to the nozzle, and valve means comprising a valve seat at an inlet of said conduit means and a stem fixedly attached at one end to a portion of a wall of the container and having a free end engageable with the valve seat to prevent entry of liquid into the conduit means from the interior of the container when the container is in an unstressed condition, said portion of the wall being movable outwardly on squeezing the container to move the stem away from the seat, thereby opening the conduit means to the interior of the container and resulting in delivery of wash liquid out through the conduit means and nozzle when the bottle is in an inverted position.

2. A wash bottle as set for in claim 1 wherein the line of movement of the free end of the stem in opening and closing the valve intersects the wall to which the other end of said stem is attached.

3. A wash bottle as set forth in claim 1 having a tube extending through said closure with the outer end of the tube comprising said nozzle and the portion of the tube inside the closure comprising said conduit means and wherein said stem is attached to a portion of a wall opposite the mouth.

4. A wash bottle as set forth in claim 3 further comprising a guide for said stem located inside the container adjacent said mouth.

5. A wash bottle as set forth in claim 4 wherein said container comprises a neck leading to said mouth, and the guide is attached to the wall of the container within said neck.

6. A wash bottle as set forth in claim 5 wherein said guide comprises a collar surrounding said stem and containing an opening therein for passage of wash liquid therethrough.

7. A wash bottle as set forth in claim 6 wherein said container is of substantially cylindrical shape and has a bottom wall at one end and a head at the other.

8. A wash bottle as set forth in claim 7 further comprising a vent for said container through which air may enter the bottle to replace wash liquid forced out of the bottle.

9. A wash bottle as set forth in claim 8 wherein said vent contains a check valve which opens to admit air during return of the container to its unstressed condition after squeezing but which closes upon squeezing the bottle so as to prevent leakage of liquid through the vent when the bottle is used in an inverted position.

10. A wash bottle as set forth in claim 9 wherein both said mouth and said vent are located on said head and said check valve comprises a ball and a seat for the ball at the outer end of the vent.

11. A wash bottle as set forth in claim 7 or 10 wherein said mouth is located on said head, the inner end of said tube is substantially parallel to the axis of the container, and the tube includes a bend therein so that the discharge end of the tube is at an angle of substantially 90° to the axis of the container.

12. A wash bottle as set forth in claim 1 wherein said mouth is on a side wall of the container and said container has a bottom wall to which said stem is attached.

13. A wash bottle as set forth in claim 12 wherein said conduit means comprises a first tubular member extending inwardly from said mouth and having a closed inner end and ports in the sidewall thereof through which liquid may pass into the interior of the bottle on filling thereof, and a sleeve attached at its outer end to the inside of the closure and adapted for a telescoping fit inside said first tubular member when the bottle is closed so as to close said ports.

14. A wash bottle as set forth in claim 13 wherein said first tubular member has an opening in the sidewall thereof spaced inwardly of the inner end of said sleeve and comprising the port for said valve and defining the seat thereof.

15. A wash bottle as set forth in claim 14 wherein said first tubular member has two openings therein aligned with said stem, the opening most remote from said bottom wall comprising said valve port and the opening nearest said bottom wall comprising a guide from said valve stem which extends therethrough.

16. A wash bottle as set forth in claim 1 wherein the discharge end of said tube has a diameter of between about 1/32" and about 3/16".

17. A wash bottle as set forth in claim 10 wherein said discharge end has a diameter of approximately 1/16".

18. A method for ameliorating hemorrhoidal conditions by removal of fecal matter from the area surrounding the anus without the use of paper or other solid state material comprising the steps of:

positioning in an inverted orientation adjacent the anal area a wash bottle comprising a container constituted of flexible resilient material having a discharge nozzle for delivery of wash liquid when the bottle is in an inverted position and an internal valve that is opened by movement of a valve stem away from a valve seat on deformation of the container by squeezing thereof and which is closed by return of the container to its original configuration in an unstressed condition;

squeezing the wash bottle so as to open the valve and deliver a stream of wash liquid out through the tube; and directing said stream of wash liquid to areas of body tissue bearing fecal matter so as to irrigate such areas and remove the fecal matter therefrom.

* * * * *